United States Patent

Ricottone

Patent Number: 5,462,711
Date of Patent: Oct. 31, 1995

[54] DISPOSABLE BEAKER SHEATH

[76] Inventor: Jacqueline L. Ricottone, 141 Promontory Dr. W., Newport Beach, Calif. 92660

[21] Appl. No.: 234,933

[22] Filed: Apr. 28, 1994

Related U.S. Application Data

[63] Continuation of Ser. No. 941,979, Sep. 8, 1992, abandoned, which is a continuation of Ser. No. 629,118, Dec. 17, 1990, abandoned.

[51] Int. Cl.$^6$ .............. A61L 2/02; A61L 2/18; A61J 1/00; B65D 30/16
[52] U.S. Cl. .............. 422/1; 422/20; 422/28; 422/102; 383/121.1; 220/404; 215/11.3
[58] Field of Search .............. 422/20, 28, 99, 422/102, 1; 383/33, 121, 121.1, 127, 902; 220/403, 404, 9.1; 134/104.1; 215/11.1, 11.3, 12.1; 53/449, 175

[56] References Cited

U.S. PATENT DOCUMENTS

| | | | |
|---|---|---|---|
| 1,886,406 | 11/1932 | Kniffin | 220/404 |
| 3,161,311 | 12/1964 | Boston | 215/11.3 |
| 3,481,687 | 12/1969 | Fishman | 422/20 |
| 3,659,825 | 5/1972 | Reiter | 366/130 |
| 3,673,868 | 7/1972 | Beury, III et al. | 73/343 R |
| 3,773,211 | 11/1973 | Bridgman | 220/403 |
| 3,807,954 | 4/1974 | McDonald | 21/87 |
| 3,834,570 | 10/1974 | Barr | 215/11.3 |
| 3,901,230 | 8/1975 | Henkin | 128/188 |
| 3,933,263 | 1/1976 | Frew et al. | 220/404 X |
| 4,108,182 | 8/1978 | Hartman et al. | 128/305 |
| 4,332,906 | 6/1982 | Taylor | 435/291 |
| 4,379,455 | 4/1983 | Deaton | 604/320 |
| 4,658,989 | 4/1987 | Bonerb | 222/105 |
| 4,756,445 | 7/1988 | Agee, Sr. | 220/40 |
| 4,813,556 | 3/1989 | Lawrence | 215/11.3 |
| 4,869,391 | 9/1989 | Farrington | 220/404 X |
| 4,878,597 | 11/1989 | Haast | 220/404 |
| 4,986,428 | 1/1991 | Signorini | 215/11.3 |
| 5,014,872 | 5/1991 | Robbins, III | 220/403 |
| 5,019,344 | 5/1991 | Kutner et al. | 422/299 X |
| 5,302,344 | 4/1994 | Perlman | 422/26 |

*Primary Examiner*—Robert J. Warden
*Assistant Examiner*—E. Leigh Dawson
*Attorney, Agent, or Firm*—Price, Gess & Ubell

[57] ABSTRACT

A method and apparatus maintains a level of sterilization during medical procedures operative upon a bacteriologically contaminated workpiece. A bacteriologically impermeable sheath is placed around the workpiece for maintaining bacteriological separation between the workpiece and medical equipment activating the medical procedure. In the preferred embodiment, the sheath lines a beaker in which dental implants, the workpieces, are placed when being cleaned using ultrasound. The sheath is cost effective enough to be disposed of after each use.

5 Claims, 1 Drawing Sheet

U.S. Patent
Oct. 31, 1995
5,462,711
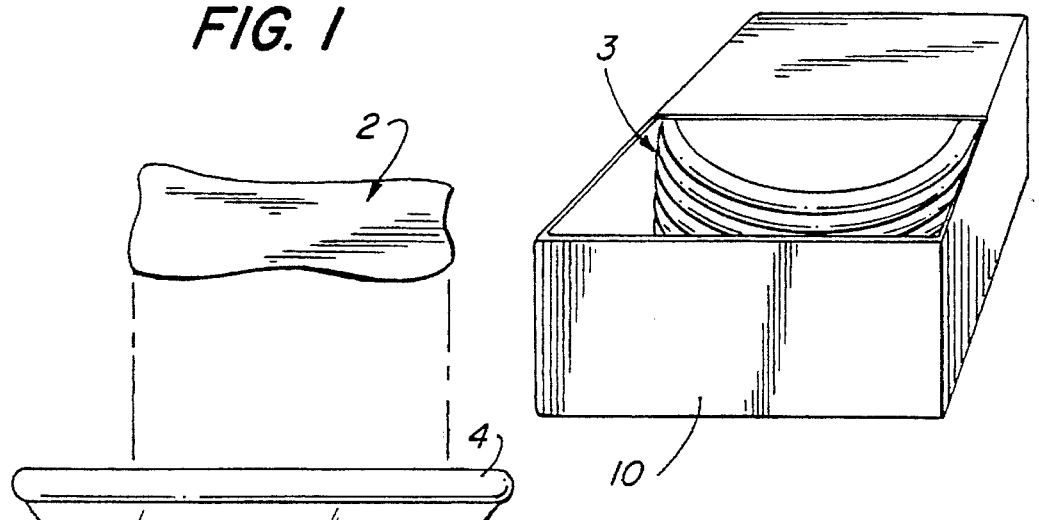
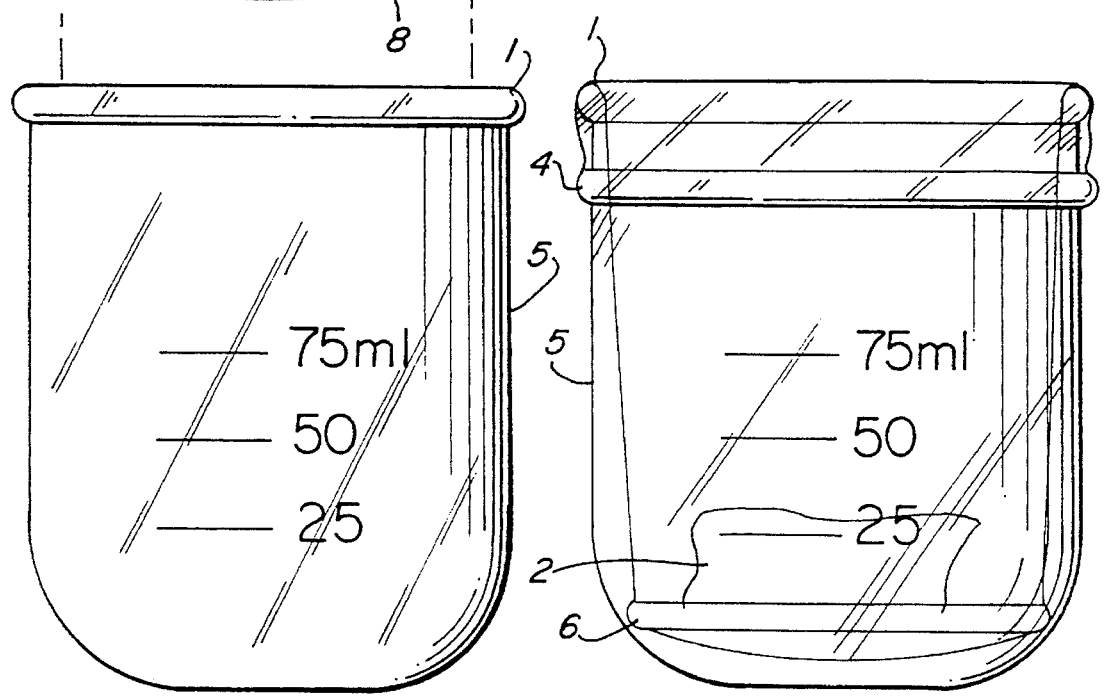

DISPOSABLE BEAKER SHEATH

This application is a continuation of Ser. No. 07/941,979, filed Sep. 8, 1992, now abandoned, which is a continuation of Ser. No. 07/629,118, filed Dec. 17, 1990, now abandoned.

FIELD OF THE INVENTION

The present invention relates to medical and dental procedures and, more particularly, to a method and apparatus usable in the aseptic maintenance of sterilization during medical and dental procedures wherein a single piece of medical equipment may be made operative with many bacteriologically contaminated workpieces.

BACKGROUND OF THE INVENTION

Presently, doctors and dentist use many processes, such as ultrasonic cleaning, in their offices. For instance, a dental appliance such as an implant or bridge, for example that needs to be cleaned may be placed in liquid in a beaker. The beaker fits inside a common ultrasonic apparatus.

During the course of the day, many appliances may need to be ultrasonically processed. For the dentist to keep one appliance from bacteriologically contaminating another, either the beaker must be disinfected after each use, or separate beakers must be used.

This becomes a very expensive and time-consuming procedure. Man hours are lost sterilizing each beaker after each use, and many beakers must be purchased in order to run an efficient procedure where many implants may be processed in a single day. Besides taking too long, a sterilization procedure cannot be used on some dental appliances such as a bridge, for example, due to the plastic materials.

Additionally, because of the direct contact of the bacteriologically contaminated implant with the inside of each beaker, the possibility of transference of germs from one implant to another is extremely high. It is very difficult to fully sterilize every beaker after every use, and any beaker which does not get fully sterilized acts as a pathway for germs and bacteria to jump from one implant or workpiece to another.

It is believed that many medical and dental practitioners try to face these problems by wrapping the implant in plastic and tossing the wrapped implant into a beaker. However, this technique is unsterile, costly, and dangerous.

The plastic bags, which are not made for these purposes, are not bacteriologically impermeable, and begin to break down or melt at higher temperature. The seams and bag openings are not always sealed, and the bags are often open pathways for germs. The beaker is filled with the same fluid throughout the day, and only the wrapped implants are exchanged. This fluid becomes contaminated and acts as a conduit for infection.

Thus, this technique is also unacceptable and may lead to the formation of bad habits such as a failing to sterilize the appliance when such sterilization is essential.

OBJECTS OF THE INVENTION

It is therefore one object of the invention to provide a method and apparatus which is cost effective and speedily allows a single piece of medical equipment to operate on a multitude of different bacteriologically contaminated appliances.

It is yet a further object of the invention to provide a method and apparatus whereby aseptic sterilization is maintained from one bacteriologically contaminated dental appliance to another, and wherein the medical equipment operative on the many appliances are protected from being itself bacteriologically contaminated.

It is yet a still further object of the invention to provide a cost effective method and apparatus for maintaining aseptic sterilization in medical equipment which is operative upon many different bacteriologically contaminated dental appliances without the need to disinfect any part of the medical equipment after each use.

SUMMARY OF THE INVENTION

These and other objects of the invention are provided for by a method and apparatus which maintains a high level of sterilization during medical procedures operative upon many bacteriologically contaminated dental appliances. A bacteriologically impermeable sheath is placed around the appliance, or between the appliance and the medical equipment environment, for maintaining bacteriological separation between the appliance and the medical equipment.

In the preferred embodiment, the sheath fits inside of and lines a beaker in which the dental appliances are placed when being cleaned using ultrasound. The sheath extends out of the beakers's top and has an elasticized member for gripping the beaker's outer circumference when in use.

The sheath has a rigid member disposed therewithin to provide form and body, and aid the easy placement of the sheath within the beaker. The sheath may be filled with fluid in which the appliance may be immersed, and is cost effective enough to be disposed of after each use.

BRIEF DESCRIPTION OF THE DRAWINGS

The present invention, both as to its organization and manner of operation, together with further objects and advantages, may be understood by reference to the accompanying drawings.

FIG. 1 is an exploded view of the preferred embodiment of the invention as used with a beaker;

FIG. 2 is an illustration of a storage container and dispenser which may be utilized with the preferred embodiment of the invention; and FIG. 3 is an illustration of the preferred embodiment of the invention interacting with a beaker.

DETAILED DESCRIPTION OF THE PREFERRED EMBODIMENT

The following description is provided to enable any person skilled in the art to make and use the invention and sets forth the best modes contemplated by the inventor of carrying out her invention. Various modifications, however, will remain readily apparent to those skilled in the art, since the generic principles of the present invention have been defined herein.

FIG. 1 illustrates an exploded view of the preferred embodiment of the invention being used in a beaker or container 1. The beaker 1 may be used to hold dental appliances 2 during ultrasonic cleaning of the appliance. The ultrasonic cleaning equipment is well known and is not shown.

In the preferred embodiment of the invention, an appliance 2 is placed inside of the beaker sheath 3.

The beaker sheath 3 is placed inside of the beaker 1, thereby becoming a liner between the beaker 1 and the appliance 2.

The beaker sheath 3 is bacteriologically impermeable, and may itself be filled with liquid (not shown).

In the preferred embodiment of the invention, the beaker sheath 3 is made from Latex® or any other suitable bacteriologically impermeable and cost effective material. Thus, the appliance 2 may be cleaned ultrasonically without contaminating the beaker 1. This eliminates the need for sterilization of the beaker and appliance.

The beaker sheath 3 may utilize a material that will allow fluid and bacteria to flow from the beaker 1 into the inside of the beaker sheath 3. However, it is imperative that there be no bacteriological exit from the inside of the beaker sheath 3.

As shown in FIG. 1, the beaker sheath 3 has an elasticized member 4 which may interact with the outside 5 of the beaker 1. This is also shown in FIG. 3. The elasticized member 4 provides a gripping action to with the outer surface 5 of the beaker 1, and thereby hold the beaker sheath 3 in place during use. A portion of sheath 3 will extend up and out and around the top edge of the beaker 1, so that the elasticized member 4 can grip the beaker 1 some distance down from the top of the beaker 1 some distance down from the to of the beaker 1.

The sheath 3 includes a rigid support member 6 which divides the sheath wall 7 from the sheath bottom 8. When in use, the rigid member 6 anchors the sheath at the bottom of the beaker 1, thereby extending the sheath 3 for use. The rigid member 6 also provides body to the sheath 3, thereby allowing easy installation of the sheath when used.

Both the rigid member 6 and the elasticized member 4 are formed into the sheath 3 in an O-ring shape. The rigid member 6 will have a smaller radial diameter than the elasticized member 4, thereby allowing both a conservation of space during storage and an easy installation when used.

The rigid member 6 and the elasticized member 4 may be made from the same Latex® or other bacteriologically impermeable material as the beaker sheath wall 7 and the beaker sheath bottom 8. Generally, the beaker sheath 3 is a flexible membrane material which is both cost effective and disposable.

FIG. 2 illustrates a storage container and dispenser 10 which contains multiple beaker sheaths 3. The beaker sheaths 3 may be individually wrapped and sealed or, as shown, they may merely be placed one on top of another for dispensing. The sheaths, when individually wrapped and sealed especially when used with such a dispenser, provide individual doctors and dentists with an easy and cost effective method and apparatus for maintaining aseptic sterilization when using a single piece of medical equipment with a plurality of appliances in a short amount of time. This is especially apparent in the cleaning of dental appliances such as implants or bridges, for example with ultrasound.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. An apparatus for maintaining an aseptic chain of sterility during medical cleaning of a bacteriologically contaminated appliance in an ultrasonic cleaning machine, the apparatus comprising:

a rigid cylindrical container having an open top, side walls, and a closed base end;

a disposable, bacteriologically impermeable sheath formed of a flexible material, the sheath having an open end provided with elastic means for gripping an outer upper periphery of the top of the container when the sheath is inserted therein, a closed end connected to the open end by a substantially cylindrical side wall and having a rigid O-ring-shaped member formed peripherally around the closed end to facilitate insertion of the sheath into the container, with the open end of the sheath being detachably closely fitted by the elastic means over the outer upper periphery of the open top of the container, the closed end of the sheath being disposed adjacent to an inner surface of the closed base end of the container, the rigid O-ring-shaped member being disposed substantially in contact with a juncture between the closed base end inner surface of the container and an inner surface of the sidewalls of the container; and a sterilizing liquid filling the sheath, the liquid covering an appliance disposed within the sheath to be medically cleaned.

2. A method for maintaining an aseptic chain of sterility during medical cleaning of a bacteriologically contaminated appliance in an ultrasonic cleaning machine, the method comprising the steps of:

(a) providing a cylindrical container having an open mouth, sidewalls and a closed base end;

(b) providing a disposable, bacteriologically impermeable sheath formed of a flexible material, the sheath having an open end and a closed end connected by a substantially cylindrical side wall, and having a rigid O-ring-shaped member formed peripherally around the closed end, the open end being elastic;

(c) inserting the sheath into the container by closely fitting the elastic open end of the sheath over an outer upper periphery of the open mouth of the container, and disposing the closed end of the sheath adjacent to an inner surface of the closed base end of the container, the rigid O-ring-shaped member being disposed substantially in contact with a juncture between the closed base end inner surface of the container and an inner surface of the sidewalls of the container;

(d) inserting an appliance to be cleaned into the sheath, the appliance being bacteriologically isolated from the container;

(e) filling the sheath with a disinfectant liquid, the liquid covering the appliance disposed within the sheath;

(f) ultrasonically agitating the appliance to clean the appliance;

(g) removing the appliance from the sheath; and (h) discarding the sheath and the liquid.

3. A method for maintaining sterility of a container during processing of a medical item disposed in the container, the method comprising the steps of:

(a) providing a cylindrical container having an open mouth and a closed base end;

(b) providing a disposable, bacteriologically impermeable sheath formed of a flexible material, the sheath having an open end and a closed end connected by a substantially cylindrical side wall, having a rigid O-ring-shaped member formed peripherally around the closed end, the open end being elastic;

(c) inserting the disposable sheath into the container with the open end of the sheath closely fitted over an outer upper periphery of the open mouth of the container, and disposing the closed end of the sheath adjacent to an inner surface of the closed base end of the container, the rigid O-ring-shaped member being disposed substantially in contact with a juncture between the closed base end inner surface of the container and an inner surface of the sidewalls of the container;

(d) placing an item to be processed into the disposable sheath, the item being isolated from the container by the sheath;

(e) processing the item including covering the item with a disinfectant liquid;

(f) removing the processed item from the sheath;

(g) discarding the sheath and liquid; and (h) repeating steps (b)–(h) with a new sheath if an additional item is to be processed.

4. An apparatus for maintaining an aseptic chain of sterility during medical cleaning of a bacteriologically contaminated appliance in an ultrasonic cleaning machine, said apparatus comprising:

a container having an open top end and a closed bottom end joined by sidewalls substantially perpendicular to said bottom end;

a bacteriologically impermeable sheath having an open end and a closed end, formed from a flexible material, the sheath's closed end disposed in proximity to the bottom end of the container and the sheath's open end coincident with the open end of the container, said sheath including a rigid O-ring-shaped member located towards the closed end of said sheath for providing shape to the sheath when in place in the container; and a disinfectant liquid within said sheath covering said appliance, when placed inside said sheath.

5. The apparatus of claim 4 wherein said rigid O-ring-shaped member is made from the same material as the sheath wall and integral with said wall.

* * * * *